United States Patent
Biagini et al.

(10) Patent No.: US 6,861,543 B2
(45) Date of Patent: Mar. 1, 2005

(54) PROCESS FOR THE PREPARATION OF EP(D)M ELASTOMERIC COPOLYMERS AND TERPOLYMERS

(75) Inventors: Paolo Biagini, Trecate-Novara (IT); Stefano Ramello, Novara (IT); Roberto Provera, Vercelli (IT); Roberto Santi, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/476,884

(22) PCT Filed: Apr. 23, 2002

(86) PCT No.: PCT/EP02/04533
§ 371 (c)(1),
(2), (4) Date: Apr. 21, 2004

(87) PCT Pub. No.: WO02/092609
PCT Pub. Date: Nov. 21, 2002

(65) Prior Publication Data
US 2004/0167017 A1 Aug. 26, 2004

(30) Foreign Application Priority Data
May 17, 2001 (IT) .................................. MI2001A1017

(51) Int. Cl.[7] .......................... C07F 17/00; B01J 31/00; C08F 4/44
(52) U.S. Cl. .......................... 556/53; 502/103; 502/117; 526/160; 526/943
(58) Field of Search .......................... 556/53; 502/103, 502/117; 526/160, 943

(56) References Cited

U.S. PATENT DOCUMENTS

| | | | |
|---|---|---|---|
| 6,124,413 A | | 9/2000 | Banzi et al. ............... 526/160 |
| 6,211,110 B1 | * | 4/2001 | Santi et al. ............... 502/152 |
| 6,596,891 B1 | * | 7/2003 | Sommazzi et al. ......... 556/181 |

FOREIGN PATENT DOCUMENTS

| | | |
|---|---|---|
| EP | 0 806 436 | 11/1997 |
| EP | 0 955 304 | 11/1999 |
| EP | 1 013 675 | 6/2000 |

* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

A process is described for the preparation of elastomeric EP(D)M copolymers and terpolymers, characterized in that it is carried out in the presence of metallocene compounds of general formula (I) having a racemic stereoisomerism

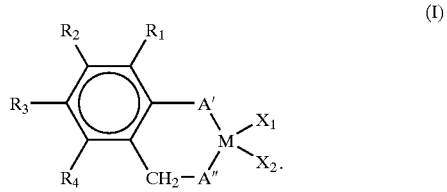

31 Claims, No Drawings

PROCESS FOR THE PREPARATION OF EP(D)M ELASTOMERIC COPOLYMERS AND TERPOLYMERS

The present invention relates to a process for the production of ethylene-propylene (EPR) elastomeric copolymers, particularly with a high propylene content, and ethylene-propylene-diene (EPDM) elastomeric terpolymers, particularly with a high diene content.

It is well known that the above (co) or (ter) polymerizations are increasingly developing zirconium or titanium complexes carrying ligands of the bis-indenyl, bisfluorenyl or mixed type, such as fluorenyl cyclopentadienyl ligands (see P. C. Mohring, N. J. Coville, J. Organometal. Chem. 479, 1, 1994).

These catalysts, however, have the disadvantage of not always producing a Mooney viscosity ($ML_{1+4}$ at 100° C.) which is acceptable from an applicative point of view, in particular in the preparation of ethylene-propylene elastomeric copolymers with a propylene content ranging from 35 to 65% by weight, a composition range which gives the best results in terms of elastomeric properties.

It is not always easy, moreover, to obtain ethylene-propylene-diene (EPDM) terpolymers with a diene content higher than 10% by weight. In this respect, EP-A-347,129 describes a process for the production of high molecular weight EPDM elastomeric terpolymers in the presence of a metallocene-alumoxane catalytic system. The terpolymers prepared according to this catalytic system never exceed a diene content of 8.9% by weight, as illustrated in the examples of the above patent application.

EP-A-955,304 describes a family of metallocene compounds with a bridged structure, useful in the preparation of α-olefin (co)polymers.

It has now been found that, among the metallocenes described in the above patent application, some of which having a stereoisomerism of the racemic type, are particularly suitable for the preparation of polymers of the EP(D)M type with a high propylene and/or diene content.

In accordance with this, the present invention relates to metallocene compounds of general formula (I) having a racemic stereoisomerism

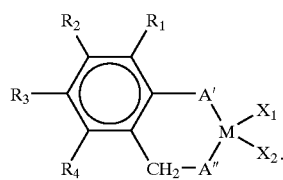

(I)

wherein

M is selected from titanium, zirconium, hafnium, preferably from zirconium and hafnium;

$X_1$ and $X_2$, the same or different, are selected from halogen, amide, carboxy, alkoxy, carbamate, alkyl, aryl, hydrogen; they are preferably selected from halogen, a $C_1$–$C_7$ hydrocarbyl radical, hydrogen; they are even more preferably chlorine;

A' and A", the same or different, are a radical of the $\eta^5$-tetrahydroindenyl type (Ia):

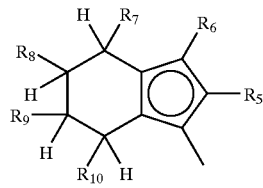

(Ia)

wherein the groups $R_5$, $R_6$, $R_7$, $R_8$, $R_9$, $R_{10}$, the same or different, are selected from hydrogen, a $C_1$–$C_8$ aliphatic, $C_5$–$C_{12}$ cycloaliphatic, $C_6$–$C_{14}$ aryl radical, preferably from hydrogen, methyl, ethyl, phenyl;

the groups $R_1$, $R_2$, $R_3$, $R_4$, the same or different, are selected from hydrogen, a $C_1$–$C_8$ aliphatic, $C_5$–$C_{12}$ cycloaliphatic, $C_6$–$C_{14}$ aryl radical, halogen; they are preferably hydrogen, methyl, benzyl, fluorine, even more preferably hydrogen.

The reaction between anions of cyclopentadienyl, indenyl or fluorenyl ligands and the salts of transition metals generally produce metallocenes which are achiral or having various types of stereoisomerism in relation to the symmetry of the ligands with which the reaction is carried out. In particular, ligands of the bridged bis-indenyl type, with the bridge bound in positions 1 and 1', respectively, when used in the formation of metallocenes of Group 4, can cause the formation of rac- and meso- bis(indenyl)metal dichlorides, as the π faces of each 1-substituted indenyl ligand are enantiotopic. In this document, the planar chirality of the described complexes follows the definition of R. L. Halterman contained in "Metallocenes synthesis reactivity applications". A. Togni and R. L. Halterman editors, wiley-VCH, Weinheim (1998), volume 1, pages 456–469. According to this definition, the planar chirality R or S is assigned on the basis of the configuration, according to Cahn-Ingold-Prelog, of the carbon atom in position 1 of the ligand and considering the metal as individually bound to all five carbon atoms of the cyclopentadienyl ring. In this way, the chirality can be described as (p-R) or (p-s) or (1R) or (1S), to stress the fact that the definition relates to planar chirality based on position 1 of the ligand. For more details, the above concepts are illustrated in Scheme 1, which shows the various possibilities of obtaining bis-tetrahydroindenyl complexes bridged with an o-benzylidene group bound in positions 1 and 1'.

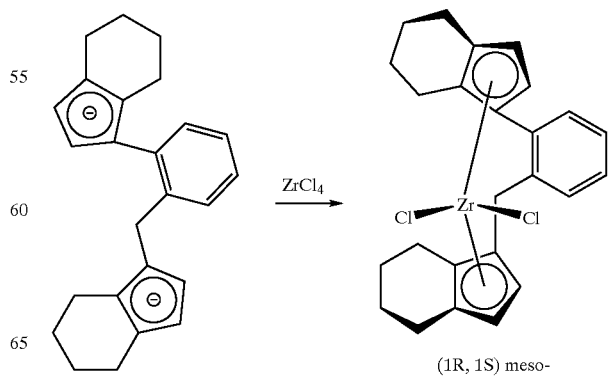

(1R, 1S) meso-

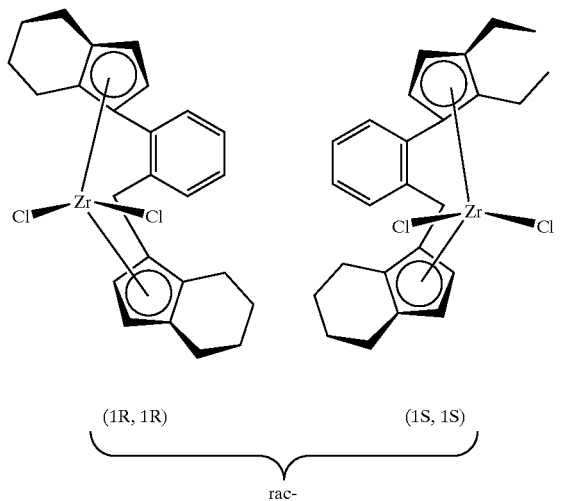

(1R, 1R)     (1S, 1S)

rac-

Scheme 1: possibility of forming meso- and rac- complexes by the reaction of $ZrCl_4$ with dianions of bis-tetrahydroindenyl ligands bridged in position 1, 1'.

A second object of the present invention relates to a process for the preparation of ethylene-propylene (EPR) elastomeric copolymers having a propylene content ranging from 15 to 75% by weight, which comprises the following steps:

(1) propylene, optionally diluted with a hydrocarbon, preferably a low-boiling $C_3$–$C_5$ hydrocarbon, even more preferably propane, is fed to a polymerization reactor, at such a pressure as to allow the use of propylene in liquefied form;

(2) ethylene is added to the mixture obtained in step (1) in a sufficient quantity to maintain the desired ethylene/propylene ratio in liquid phase;

(3) the catalytic system is added to the mixture obtained in step (2), said catalytic system comprising one or more metallocenes having general formula (I) and one or more cocatalysts selected from (i) compounds having general formula (IV) $(Ra)_xNH_{4-x}B(Rd)_4$, compounds having general formula (V) $(Ra)_3PHB(Rd)_4$ compounds having general formula (VI) $B(Rd)_3$, compounds having general formula (VII) $(C_6H_5)_3CB(Rd)_4$, optionally in the presence of an alkylating agent, (ii) an alumoxane; in the above compounds having general formula (IV), (V), (VI) or (VII), x being selected from 1, 2 or 3; the groups $R_a$, the same or different, being monofunctional alkyl or aryl groups; the groups $R_d$, the same or different, being monofunctional aryl radicals;

(4) the mixture obtained in step (3) is reacted for a sufficient time to allow the polymerization of the ethylene-propylene system to give an EPR copolymer, characterized in that the catalytic system comprises at least one metallocene having a racemic stereoisomerism, selected from those having general formula (I)

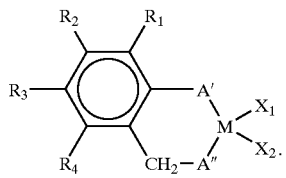

wherein

M is selected from titanium, zirconium, hafnium, preferably zirconium and hafnium;

$X_1$ and $X_2$, the same or different, are selected from halogen, amide, carboxy, alkoxy, carbamate, alkyl, aryl, hydrogen; they are preferably selected from halogen, a $C_1$–$C_7$ hydrocarbyl radical, hydrogen; they are even more preferably chlorine;

A' and A", the same or different, are a radical of the $\eta^5$-tetrahydroindenyl type (Ia):

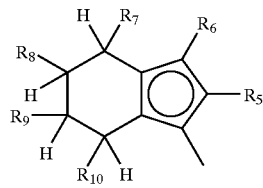

wherein the groups $R_5$, $R_6$, $R_7$, $R_6$, $R_9$, $R_{10}$, the same or different, are selected from hydrogen, a $C_1$–$C_8$ aliphatic, $C_5$–$C_{12}$ cycloaliphatic, $C_6$–$C_{14}$ aryl radical, preferably from hydrogen, methyl, ethyl, phenyl;

the groups $R_1$, $R_2$, $R_3$, $R_4$, the same or different, are selected from hydrogen, a $C_1$–$C_8$ aliphatic, $C_5$–$C_{12}$ cycloaliphatic, $C_6$–$C_{14}$ aryl radical, halogen; they are preferably hydrogen, methyl, benzyl, fluorine, even more preferably hydrogen.

The process of the present invention allows the production, if desired, of EPR copolymers with a high propylene content.

The present invention also relates to a process for the preparation of ethylene-propylene-diene (EPDM) terpolymers, which comprises the following steps:

(1) propylene and the diene, optionally diluted with a hydrocarbon, preferably a low-boiling $C_3$–$C_5$ hydrocarbon, even more preferably propane, are fed to a polymerization reactor, at such a pressure as to allow the use of propylene in liquefied form;

(2) ethylene is added to the mixture obtained in step (1) in a sufficient quantity to maintain the desired ethylene/propylene/diene ratio in liquid phase;

(3) the catalytic system is added to the mixture obtained in step (2), said catalytic system comprising one or more metallocenes having general formula (I) and one or more cocatalysts selected from (i) compounds having general formula (IV) $(Ra)_xNH_{4-x}B(Rd)_4$, compounds having general formula (V) $(Ra)_3PHB(Rd)_4$, compounds having general formula (VI) $B(Rd)_3$, compounds having general formula (VII) $(C_6H_5)_3CB(Rd)_4$, optionally in the presence of an alkylating agent, (ii) an alumoxane; in the above compounds having general formula (IV), (V), (VI) or (VII), x being selected from 1, 2 or 3; the groups $R_a$, the same or different, being monofunctional alkyl or aryl groups; the groups $R_d$, the same or different, being monofunctional aryl radicals;

(4) the mixture obtained in step (3) is reacted for a sufficient time to allow the polymerization of the ethylene-propylene-diene system to give an EPDM terpolymer;

characterized in that the catalytic system comprises at least one metallocene having a racemic stereoisomerism, selected from those having general formula (I)

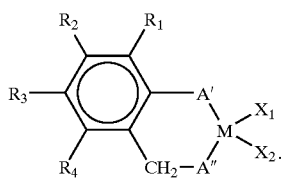

(I)

wherein
M is selected from titanium, zirconium, hafnium, preferably zirconium and hafnium;

$X_1$ and $X_2$, the same or different, are selected from halogen, amide, carboxy, alkoxy, carbamate, alkyl, aryl, hydrogen; they are preferably selected from halogen, a $C_1$–$C_7$ hydrocarbyl radical, hydrogen; they are even more preferably chlorine;

A' and A", the same or different, are a radical of the $\eta^5$-tetrahydroindenyl type (Ia):

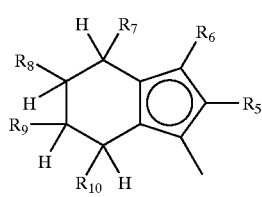

(Ia)

wherein the groups $R_5$, $R_6$, $R_7$, $R_8$, $R_9$, $R_{10}$, the same or different, are selected from hydrogen, a $C_1$–$C_8$ aliphatic, $C_5$–$C_{12}$ cycloaliphatic, $C_6$–$C_{14}$ aryl radical, preferably from hydrogen, methyl, ethyl, phenyl;

the groups $R_1$, $R_2$, $R_3$, $R_4$, the same or different, are selected from hydrogen, a $C_1$–$C_8$ aliphatic, $C_5$–$C_{12}$ cycloaliphatic, $C_6$–$C_{14}$ aryl radical, halogen; they are preferably hydrogen, methyl, benzyl, fluorine, even more preferably hydrogen.

The process of the present invention allows the production, if desired, of EPDM terpolymers having a propylene content ranging from 30 to 55% by weight, and a diene content ranging from 3 to 18% by weight, more specifically from 4 to 11% by weight.

Typical examples of metallocenes having general formula (I) which can be used in the production of EP(D)M according to the present invention are:

rac-o-benzylidenebis-($\eta^5$-1-tetrahydroindenyl)zirconium dichloride
rac-o-benzylidenebis-($\eta^5$-1-tetrahydroindenyl)zirconium dimethyl;
rac-o-benzylidenebis-($\eta^5$-1-tetrahydroindenyl)zirconium diacetate;
rac-o-benzylidenebis-($\eta^5$-1-tetrahydroindenyl)zirconium dimethoxide;
rac-o-benzylidenebis-($\eta^5$-1-tetrahydroindenyl)zirconium dihydride;
rac-o-benzylidenebis-($\eta^5$-1-tetrahydroindenyl)zirconium dibenzyl;
rac-o-benzylidenebis-($\eta^5$-1-tetrahydro-3-methylindenyl) zirconium dichloride;
rac-o-benzylidenebis-($\eta^5$-1-tetrahydro-3-phenylindenyl) zirconium dichloride;
rac-o-benzylidenebis-($\eta^5$-1-tetrahydroindenyl)titanium dichloride;
rac-o-benzylidenebis-($\eta^5$-1-tetrahydroindenyl)titanium dimethyl;
rac-o-benzylidenebis-($\eta^5$-1-tetrahydroindenyl)hafnium dichloride;
rac-o-benzylidenebis-($\eta^5$-1-tetrahydro-3-methylindenyl) hafnium dichloride;
rac-o-benzylidenebis-($\eta^5$-1-tetrahydro-3-phenylindenyl) hafnium dichloride;
rac-o-benzylidene-3-methylbis-($\eta^5$-1-tetrahydroindenyl) zirconium dichloride;
rac-o-benzylidene-3-phenylbis-($\eta^5$-1-tetrahydroindenyl) zirconium dichloride;
rac-o-benzylidene-3-methylbis-($\eta^5$-1-tetrahydroindenyl) zirconium dimethyl.

In the copolymerization of ethylene with propylene (and the possible diene), the catalytic system also comprises, in addition to the metallocene with a racemic stereoisomerism having general formula (I), another component (which we will call cocatalyst) selected from an alumoxane and compounds having general formula (IV) $(Ra)_xNH_{4-x}B(Rd)_4$ (wherein x is selected from 1, 2 or 3), or (V) $(Ra)_3PHB(Rd)_4$, or (VI) $B(Rd)_3$, or (VII) $(C_6H_5)_3CB(Rd)_4$, which, by reaction with a metallocene having general formula (I), are capable of generating catalytic systems of an ionic nature. In the above compounds having general formula (IV), (V), (VI) or (VII), the $R_a$ groups, the same or different, are monofunctional alkyl or aryl radicals, whereas the $R_d$ groups, the same or different, are monofunctional aryl radicals, preferably partially or totally fluorinated, even more preferably totally fluorinated.

As is known, the nature of the cocatalyst determines the preparation procedure of the catalytic system. A general description follows of two preparative methods of the catalytic system, both well known to experts in the field.

In accordance with a first method, the catalytic system is prepared starting from one or more metallocenes having general formula (I) and an alumoxane. The general term alumoxane indicates an aluminum compound which can have a linear or cyclic structure. The linear structure has general formula (VIII) $(R_e)_2$—Al—O—[—Al—$(R_e)$—O—]$_p$—Al $(R_e)_2$, whereas in its cyclic form, it has general formula (IX) —[—O—Al($R_e$)—O—]$_{p+2}$— wherein the various $R_e$ the same or different, are selected from H, $C_1$–$C_6$ alkyl radicals, $C_6$–$C_{18}$ aryl radicals; "p" is an integer ranging from 2 to 50, preferably from 10 to 35. If the various $R_e$ are the same, they are selected from methyl, ethyl, propyl, isobutyl, and are preferably methyl.

If the various $R_e$ are different, they are preferably methyl and hydrogen or alternatively methyl and isobutyl, hydrogen and isobutyl being preferred.

The alumoxane can be prepared according to various methods known to experts in the field. One of the methods comprises, for example, the reaction of an aluminum alkyl and/or an alkylaluminumhydride with water (gaseous, solid, liquid or bound, such as for example crystallization water) in an inert solvent, for example toluene. For the preparation of an alumoxane having different $R_e$ alkyl groups, two different aluminumtrialkyl groups ($AlR_3+AlR'_3$) are reacted with water (see S. Pasynkiewicz, Polyhedron 9 (1990) 429–430 and EP-A-302 424).

The exact nature of the alumoxane is not known, however, toluene solutions of methyl-alumoxane are commercially available, such as for example, the product Eurecene 5100 10T of Witco supplied with concentration in active aluminum, making its use extremely easy.

The catalytic system is prepared by adding a hydrocarbon solution at 10% by weight of alumoxane to the mixture of anhydrified monomers, previously charged into the polymerization reactor. The mixture is brought to the desired temperature and one or more metallocenes selected from those having general formula (I) are subsequently added in such a quantity as to obtain a total concentration ranging from $10^{-8}$ to $10^{-4}$ molar depending on its activity, and with a molar ratio aluminum/metallocene ranging from $2·10^2$ to $2·10^4$. In this way, the catalytic system is defined as "prepared in situ".

Alternatively, the metallocene, or mixture of metallocenes, can be pre-activated with the alumoxane before its use in the polymerization phase. In this case, the metallocene is dissolved in an inert hydrocarbon solvent, preferably aliphatic or aromatic, even more preferably toluene, so that its concentration ranges from $10^{-1}$ to $10^{-4}$ molar. The toluene solution of alumoxane is then added so that the molar ratio aluminum/metallocene ranges from $2·10^2$ to $2·10^4$. The components are left to react for a time ranging from a few minutes to 60 hours, preferably from 5 to 60 minutes, at a temperature ranging from $-78°$ C. to $+100°$ C., preferably from $0°$ C. to $70°$ C. This preparation procedure of the catalytic system is commonly called "preformation". At the end of the preformation time, the reaction mixture is added to the mixture of monomers previously prepared in the polymerization reactor, so that the final concentration of the metallocene in the reaction mixture ranges from $10^{-8}$ to $10^{-4}$ moles/litre.

In accordance with a second method, the catalytic system is prepared starting again from one or more metallocenes having general formula (I) and a cocatalyst having general formula (IV), (V), (VI) or (VII). The operating procedure, in this case, depends on the nature of the X groups bound to M in general formula (I).

With X equal to H or an alkyl radical, the catalytic system is prepared by adding one or more metallocenes having general formula (I) to the mixture of monomers previously prepared so that the total concentration ranges from $10^{-8}$ to $10^{-4}$ moles/litre. The mixture is brought to the desired temperature and a compound selected from those having general formula (IV), (V), (VI) or (VII) is subsequently introduced as cocatalyst, as described in EP-A-277,004, in such a concentration that the total molar ratio cocatalyst/metallocene ranges from 0.7 to 3.5.

With X different from H or a hydrocarbyl radical, the catalytic system is made up of one or more metallocenes having general formula (I), an alkylating compound selected from aluminum trialkyl, magnesium dialkyl and lithium alkyl, or other alkylating agents well known to experts in the field, and any of the compounds having general formula (IV), (V), (VI) or (VII), or one of their mixtures, as described in EP-A-612,769. The formation procedure of the catalytic system comprises the premixing of the metallocene compound having general formula (I) with an appropriate alkylating agent in hydrocarbon solvents, aliphatic or aromatic or their mixtures, at a temperature ranging from $-20$ to $+100°$ C., preferably from $0°$ C. to $60°$ C. and even more preferably from $+20°$ C. to $+50°$ C., for a time varying from 1 minute to 24 hours, preferably from 2 minutes to 12 hours, even more preferably from 5 minutes to 2 hours.

The molar ratio between alkylating compound and the compound having general formula (I) can vary from 1 to 1000, preferably from 10 to 500, even more preferably from 30 to 300.

The mixture is then put in contact with a compound having general formula (IV), (V), (VI) or (VII) at the above temperature for a time ranging from 1 minute to 2 hours, preferably from 2 minutes to 30 minutes, and is subsequently fed to the polymerization reactor. The molar ratio between the compound having general formula (IV), (V), (VI) or (VII) and the metallocene (I) can vary from 0.1 to 10, preferably from 1 to 3.

Regardless of the method used for the preparation of the catalytic system, the reaction between the metallocene having general formula (I) and cocatalyst can be carried out in the presence of or without varying quantities of one or all of the monomers to be polymerized. If small quantities of monomers to be polymerized are present, i.e. with molar ratios monomer/metallocene ranging from 10 to 1000, what is known in the art as prepolymerization takes place, in which small quantities of solid polymer are formed, which almost totally englobe the components of the catalytic system. This polymer suspension/catalytic system still has a high catalytic activity and can be used to polymerize high quantities of monomers with an improvement in the morphological characteristics of the polymer obtained.

The catalytic systems of the present invention are generally used in very low molar concentrations, ranging from $10^{-8}$ to $10^{-4}$, expressed in metallocene having general formula (I). Although they are very diluted, these catalytic systems are characterized by an extremely high activity, ranging from 500 to 10,000 Kg of polymer per gram of transition metal per hour of copolymerization. To obtain these activities at the above concentrations, however, it is necessary to accurately protect the catalytic system from any poisons possibly present, also in parts per million, in the monomers, above all propylene, and in the solvents used in the polymerization reaction.

This result can be obtained by using, in the polymerization environment, substances which are particularly effective in eliminating impurities characterized by the presence of active hydrogens, such as aluminum trialkyls, in particular aluminum trimethyl, aluminum triethyl, aluminum triisobutyl and aluminum diisobutylmonohydride. These substances do not directly take part in the catalytic process but are capable of effectively capturing the above poisons if used in concentrations of about $10^{-3}$ to $10^{-4}$ molar in the polymerization environment.

The catalytic system of the present invention can be applied to polymerization in slurry phase (where a dispersing agent is used, for example propane or butane) and to polymerization essentially carried out in the absence of a solvent (such as polymerization without a solvent in liquid phase). The catalyst of the invention can obviously be applied to polymerization carried out in continuous or batchwise.

When operating batchwise, the reaction time, in relation to the temperature and concentration, generally ranges from 10 minutes to 10 hours, preferably from 30 minutes to 120 minutes.

The polymerization temperature is approximately within the range of $-78°$ C. to $200°$ C., preferably from $-20°$ C. to $100°$ C., even more preferably from $10°$ C. to $70°$ C. There are no particular limitations with respect to the olefin pressure in the reaction system, even if the pressure preferably ranges from atmospheric pressure to 5 MPa.

In the polymerization process, the molecular weight can be controlled with any known method, for example, by suitably selecting the polymerization temperature and pressure or by introducing hydrogen.

At the end of the polymerization process, the elastomer produced, when leaving the reactor, is recovered in various ways, for example by subjecting it to a stripping treatment, preferably with water in a vapour stream, in order to remove non-converted monomers and the optional diluent. This operation can be followed by treatment in an extruder to remove water and possible residual traces of olefins.

In the case of the preparation of EPDM, the dienes used for the preparation of EPDM terpolymers are selected from:
  dienes with a linear chain such as such as 1,4-hexadiene and 1,6-octadiene;
  branched dienes such as 5-methyl-1,4-hexadiene, 3,7-dimethyl-1,6-octadiene, 3,7-dimethyl-1,7-octadiene;
  dienes with a single ring such as 1,4-cyclohexadiene, 1,5-cyclo-octadiene; 1,5-cyclododecadiene;
  dienes having bridged, condensed rings such as dicyclopentadiene; bicyclo[2.2.1]hepta-2,5-diene; alkenyl, alkylidene, cycloalkenyl and cycloalkylidene norbornenes such as 5-methylene-2-norbornene 5-ethylidene-2-norbornene (ENB), 5-propenyl-2-norbornene.

Among non-conjugated dienes typically used for preparing these copolymers, dienes containing at least one double bond in a tensioned ring are preferred, even more preferably 5-ethylidene-2-norbornene (ENB), and also 1,4-hexadiene and 1,6-octadiene.

The following examples are provided for a better understanding of the present invention.

EXAMPLES

In the following examples, the analytical techniques and characterization methods listed and briefly described below, were used.

The characterization by means of $^1$H-NMR and $^{13}$C-NMR spectroscopy, mentioned in the following examples, was carried out on a nuclear magnetic resonance spectrometer mod. Bruker MSL-300.

The characterization of the complexes, by means of mass spectrometry, was carried out using an inverse geometry double focus spectrometer mod. Finnigan Mat 8400.

The molecular weight measurement of the olefinic polymers was effected by means of Gel-Permeation Chromatography (GPC). The analyses of the samples were carried out in 1,2,4-trichlorobenzene (stabilized with Santonox) at 135° C. with a WATERS 150-CV chromatograph, using a Waters differential refractometer as detector.

The chromatographic separation was obtained with a set of µ-Styragel HT columns (Waters) of which three with pore dimensions of $10^3$, $10^4$, $10^5$ Å respectively, and two with pore dimensions of $10^6$ Å, establishing a flow-rate of the eluant of 1 ml/min.

The data were obtained and processed by means of Maxima 820 software version 3.30 (Millipore); the number ($M_n$) and weight ($M_w$) average molecular weight calculation was carried out by universal calibration, selecting polystyrene standards with molecular weights within the range of 6,500,000–2,000, for the calibration.

The determination of the content of units deriving from propylene and from the optional diene in the polymers is effected (according to a method of the Applicant) by means of IR on the polymers in the form of films having a thickness of 0.2 mm, using an FTIR Perkin-Elmer spectrophotometer, model 1760. The intensity is measured of the peaks characteristic of propylene at 4390 cm$^{-1}$ and ENB at 1688 cm$^{-1}$, respectively, relating to the peak at 4255 cm$^{-1}$, and the quantity determined using a standard calibration curve During the preparations described in the examples, the following commercial reagents were used:

| | |
|---|---|
| n-butyl-lithium (LiBu) 1.6 M in hexane | ALDRICH |
| zirconium tetrachloride (ZrCl$_4$) | FLUKA |
| hafnium tetrachloride (HfCl$_4$) | STREM |
| methylalumoxane (MAO) (Eurecene 5100 10T, 10% weight/volume of Al in toluene) | WITCO |
| platinum dioxide (PtO$_2$) | ALDRICH |
| Molecular sieves (3A) | ALDRICH |

The reagents and/or solvents used and not listed above are those commonly adopted in laboratories and on an industrial scale and can be easily found at the usual commercial operators specialized in the field.

Example 1

Synthesis of o-benzylidenebis-(η$^5$-1-1-indenyl)-zirconium dichloride (III)

There are several variations in the procedure described herein with respect to that indicated in EP-A-955,304.

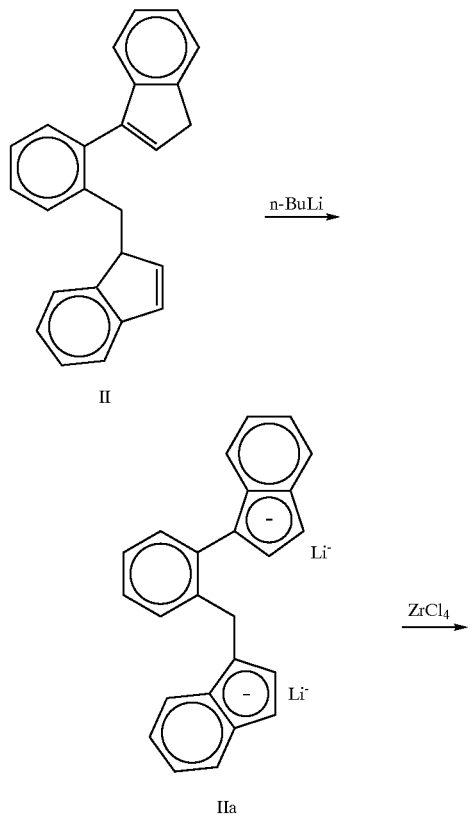

-continued

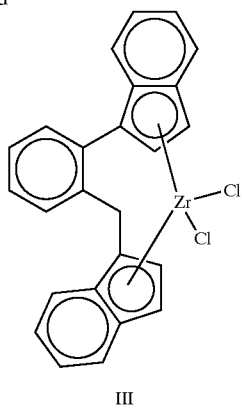

III 3.01 g of ligand having formula (II) (9.4 mmoles), obtained as described in EP-A-955,304, and 50 ml of anhydrous ethyl ether are charged in an atmosphere of argon, into a 100 ml tailed test-tube, equipped with a magnetic stirrer. 14 ml of LiBU (1.6 M in hexane) (22.4 mmoles) are added dropwise, at room temperature, to the light yellow solution thus obtained, and the mixture is kept under stirring for about 12 h. At the end, the volume of the reaction mixture is reduced to about 10 ml, most of the solvent being removed at reduced pressure, and 30 ml of anhydrous n-hexane are subsequently added. A suspension is immediately formed, which is filtered; the solid is collected and subsequently washed with n-hexane (3×10 ml). It is dried under vacuum (about 10 Pa) and the dilithium derivative having formula (IIa) thus obtained, is transferred, under an argon atmosphere, to a 100 ml tailed test-tube containing 50 ml of anhydrous toluene. 2.69 g of $ZrCl_4$ (11.5 mmoles) are added to the suspension thus obtained and the reaction mixture is then left under stirring at room temperature for about 16 h, after which it is filtered on a porous septum and the mother liquor containing the desired product is collected. The residue is washed again with toluene (3×10 ml) and the washing water is joined to the mother liquor. The toluene solution thus obtained is dried, the solvent is eliminated at reduced pressure, and the yellow solid obtained is further dried under vacuum (10 Pa) for 6 h. 3.02 g of o-benzylidenebis-($\eta^5$-1-indenyl)-zirconium dichloride (III) are thus obtained (67% yield). NMR analysis indicates that two isomers (meso- and rac-) are present in the product in a ratio of about 50/50.

$^1$-H-NMR (CDCl$_3$, δ ppm rel. to TMS): rac-isomer: 4.42 (1H, d, J 17.07), 4.66 (1H, d, J 17.06), 5.69 (1H, d, J 3.45), 6.50 (1H, d, J 3.30), 6.52 (1H, d, J 3.49), 6.64 (1H, d, J 3.49), 7.10–7.40 (8H, m), 7.40–7.70 (4H, m); meso-isomer: 4.58 (2H, s), 6.27 (1H, d, J 3.48), 6.68 (1H, d, J 2.96), 6.74 (1H, d, J 3.53), 6.82 (1H, d, J 3.45), 7.10–7.40 (m, 8H), 7.40–7.70 (4H, m).

DCI-MS: m/z 478 (negative ions, peak with the highest cluster intensity).

Example 2
Preparation of rac-o-benzylidenebis-($\eta^5$-1-indenyl) zirconium dichloride (IIIr) and meso-o-benzylidenebis-biz-($\eta^5$-1-indenyl)zirconium dichloride (IIIm).

2.40 g of complex (III) (5 mmoles) in which two isomers (meso- and rac-) are present in a ratio of about 50/50, obtained as described in example 1, and 10 ml of toluene are charged, in an argon atmosphere, into a 100 ml tailed test-tube, equipped with a magnetic stirrer. The suspension is filtered and the solid collected is dried under vacuum (about 10 Pa). 0.6 g of rac-o-benzylidenebis-($\eta^5$-1-indenyl) zirconium dichloride (IIIr) are thus obtained, having a stereo-isomeric purity of 95%, determined by means of $^1$H-NMR.

The solvent is removed from the filtrate at reduced pressure and the residual solid is dried under vacuum (10 Pa). 1.8 g of meso-o-benzylidene-bis-($\eta^5$-1-indenyl) zirconium dichloride (IIIm) are thus obtained, having a stereoisomeric purity of 67%, determined by means of $^1$H-NMR.

Example 3
Synthesis of rac-o-benzylidenebis-($\eta^5$-1-tetrahydroindenyl) zirconium dichloride (IVr).

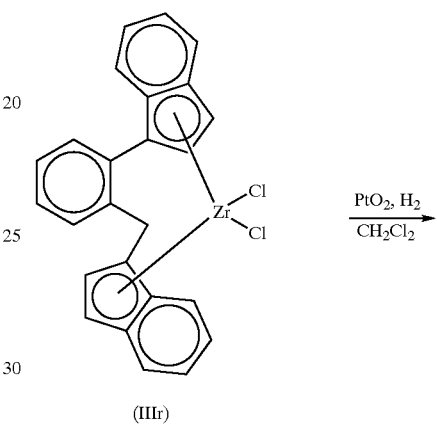

(IIIr)

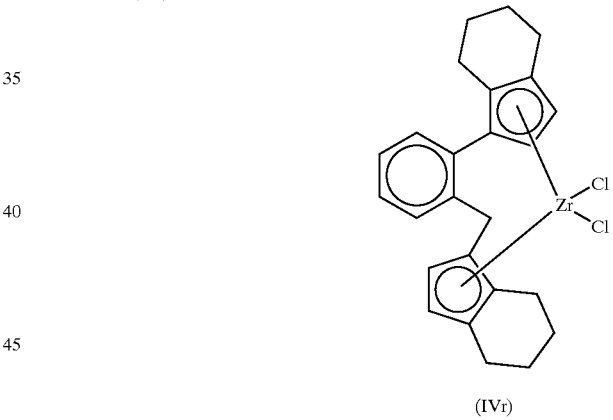

(IVr)

The following products are charged in order into a 80 ml steel autoclave: 1.13 g of rac-o-benzylidenebis-($\eta^5$-1-indenyl)zirconium dichloride (IIIr) (2.4 mmoles), 0.047 g of PtO$_2$ (0.2 mmoles), 1 g of molecular sieves (3A) and 30 ml of CH$_2$Cl$_2$. Maintaining the equipment at room temperature, hydrogen is charged up to a pressure of 0.5 MPa; the mixture is left under stirring for about 3 h, care being taken that the hydrogen pressure is kept constant. At the end, the suspension is filtered and the mother liquor recovered. The solvent is completely removed at reduced pressure and 30 ml of n-hexane are added to the residual solid; any possible insoluble products are removed by filtration, the solvent is then removed at reduced pressure and the light yellow-coloured residual solid is dried under vacuum (10 Pa) for 12 h. 0.80 g of rac-o-benzylidenebis-($\eta^5$-1-tetrahydroindenyl) zirconium dichloride (IVr) are obtained (yield 70%), having a stereo-isomeric purity of 95%, determined by means of $^1$H-NMR.

$^1$H-NMR (CDCl$_3$, δ ppm rel. to TMS): 1.5–3.3 (16H, m), 3.84 (1H, d, J 17.26), 4.06 (1H, d, J 17.25), 5.37 (1H, d, J 3.14 Hz), 5.83 (1H, d, J3.18 Hz), 6.09 (1H, d, J3.13 Hz), 6.32 (1H, d, J3.16 Hz), 7.30–7.41 (4H, m).

DCI-MS: m/z 486 (negative ions, peak with the highest cluster intensity).

Example 4
Synthesis of meso-o-benzylidenebis-(η$^5$-1-tetrahydroindenyl)zirconium dichloride (IVm).

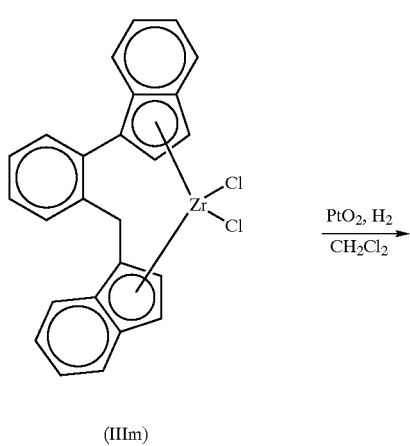

(IIIm)

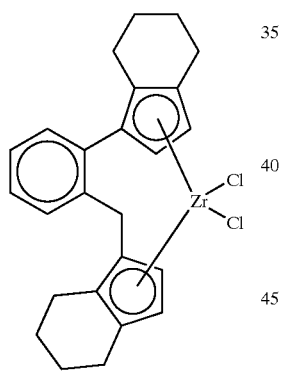

(IVm)

The following products are charged in order into a 80 ml steel autoclave: 1.13 g of meso-o-benzylidenebis-(η$^5$-1-indenyl)zirconium dichloride (IIIm) (2.4 mmoles), 0.048 g of PtO$_2$ (0.2 mmoles), 1 g of molecular sieves (3A) and 30 ml of CH$_2$Cl$_2$. Following a completely analogous procedure to that described in example 3, at the end 0.83 g of meso-o-benzylidenebis-(η$^5$-1-tetrahydroindenyl) zirconium dichloride (IVm) are obtained (yield 72%), having a stereo-isomeric purity of 80%, determined by means of $^1$H-NMR.

$^1$H-NMR (CDCl$_3$, δ ppm rel. to TMS): 1.5–3.3 (16H, m), 3.89 (2H, s), 5.62 (1H, d, J=3.30 Hz), 5.99 (1H, d, J=3.15 Hz), 6.13 (1H, d, J=3.24 Hz), 6.40 (1H, d, J=3.13 Hz), 7.20–7.40 (4H, m).

DCI-MS: m/z 486 (negative ions, peak with the highest cluster intensity).

Example 5

Synthesis of rac-o-benzylidenebis-(1-η$^5$-(3-methyl)-indenyl)hafnium dichloride (VIr) and meso-o-benzylidenebis-(1-η$^5$-(3-methyl)-indenyl)hafnium dichloride (VIm).

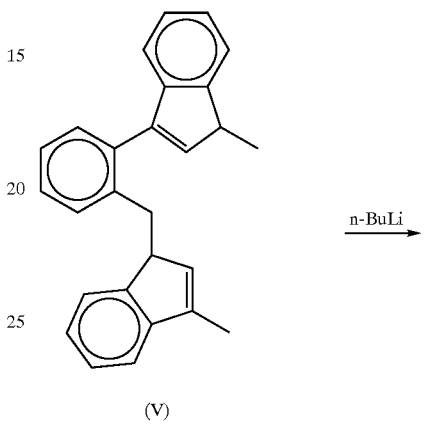

(V)

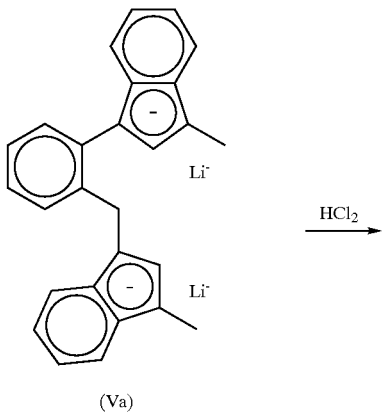

(Va)

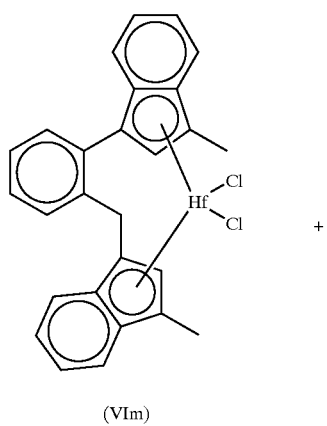

(VIm)     +

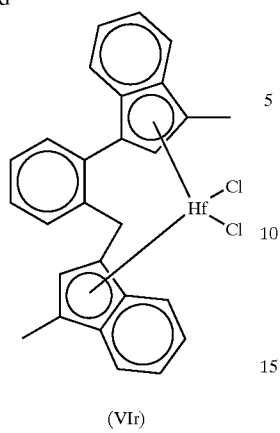

(VIr)

1.84 g of ligand having formula (V) (5.3 mmoles), obtained as described in EP-A-955,304, and 50 ml of anhydrous ethyl ether are charged in an atmosphere of argon, into a 100 ml tailed test-tube, equipped with a magnetic stirrer. 7.4 ml of LiBu (1.6 M in hexane) (11.8 mmoles) are added dropwise, at room temperature, to the yellow solution thus obtained, and the mixture is kept under stirring for about 36 h. The suspension of a white solid in a red liquid phase is obtained. The volume of the reaction mixture is reduced to about 10 ml, most of the solvent being removed at reduced pressure, and 30 ml of anhydrous n-hexane are subsequently added. The suspension is filtered and the solid collected is washed with hexane (3×10 ml). It is dried under vacuum (about 10 Pa) and the dilithium derivative having formula (Va) thus obtained, is transferred, under an argon atmosphere, to a 100 ml tailed test-tube containing 50 ml of anhydrous toluene. 1.9 g of HfCl$_4$ (5.9 mmoles) are added to the suspension thus obtained and the reaction mixture is then left under stirring at room temperature for about 16 h, after which it is filtered on a porous septum and the mother liquor containing the desired product is collected. The residue is washed again with toluene (3×30 ml) and the washing water is joined to the mother liquor. The toluene solution thus obtained is dried and the solvent is eliminated at reduced pressure. A yellow oil is obtained, to which 100 ml of ethyl ether are added. The suspension of a yellow solid in a yellow liquid phase is obtained. The solid is recovered by filtration on a porous septum and washed with hexane (3×10 ml) and then dried under vacuum (10 Pa) for 8 h. 1.29 g of rac-o-benzylidenebis(1-η$^5$-(3-methyl)-indenyl)hafnium dichloride (VIr) are thus obtained. NMR analysis indicates that there is 75% of racisomer in the product. The volume of the ether solution recovered is reduced to about 10 ml, by removing the solvent at reduced pressure, after which 50 ml of anhydrous hexane are added. A suspension is immediately formed, which is filtered, the solid is collected and subsequently washed with n-hexane (3×10 ml). It is dried under vacuum (about 10 Pa) and 0.57 g of meso-o-benzylidenebis-(1-η$^5$-(3-methyl)indenyl)hafnium dichloride (VIm) are thus recovered. NMR analysis indicates that there is 65% of meso- isomer in the product.

In this way, a total of 1.86 g of meso-o-benzylidenebis-(1-η$^5$-(3-methyl)-indenyl)hafnium dichloride and rac-o-benzylidenebis-(1-η$^5$-(3-methyl)-indenyl) hafnium dichloride are recovered with a total yield of 59%.

$^1$H-NMR (CDCl$_3$, δ ppm rel. to TMS): meso-isomer: 2.47 (s, 3H), 2.56 (s, 3H), 4.60 (d, 1H, J=17.20), 4.77 (d, 1H, J=17.21), 5.84 (s, 1H), 6.34 (s, 1H), 7.10–7.40 (m, 4H), 7.40–7.70 (m, 8H); rac-isomer: 2.23 (s, 3H), 2.33 (s, 3H), 4.48 (d, 1H, J=16.92), 4.72 (d, 1H, J=16.92), 5.49 (s, 1H), 6.27 (s, 1H), 7.10–7.40 (m, 4H), 7.40–7.70 (m, 8H).

DCI-MS: m/z 596 (negative ions, peak with the highest cluster intensity).

Example 6

Synthesis of rac-o-benzylidenebis-[1-η$^5$-(3-methyl)-tetrahydroindenyl)hafnium dichloride (VIIr).

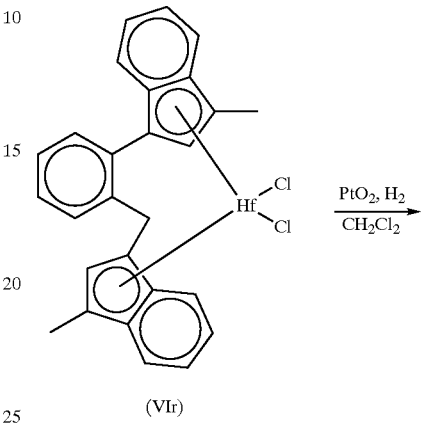

(VIr)

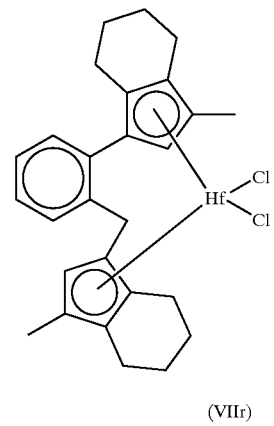

(VIIr)

The following products are charged in order into a 80 ml steel autoclave: 0.86 g of rac-o-benzylidenebis-1-η$^5$-(3-methyl)-indenyl)hafnium dichloride (VIr) (1.4 mmoles), prepared according to example 5, 0.046 g of PtO$_2$ (0.2 mmoles), 1 g of molecular sieves (3A) and 30 ml of toluene. Maintaining the equipment at room temperature, hydrogen is charged up to a pressure of 0.5 MPa; the mixture is left under stirring for about 3 h, care being taken that the hydrogen pressure is kept constant. At the end, the suspension is filtered and the mother liquor recovered. The solvent is completely removed at reduced pressure and 30 ml of n-hexane are added to the residual solid; any possible insoluble products are removed by filtration, the solvent is then removed at reduced pressure and the very light yellow-coloured residual solid is dried under vacuum (10 Pa) for 24 h. 0.56 g of rac-o-benzylidenebis-[1-η$^5$-(3-methyl) tetrahydroindenyl)hafnium dichloride (VIIr) are obtained (yield 65%), having a stereo-isomeric purity of 75%, determined by means of $^1$H-NMR.

$^1$H-NMR (C$_6$D$_6$, δ ppm rel. to TMS): meso-isomer: 1.2–3.3 (16H, m), 2.02 (3H, s), 2.24 (3H, s), 3.51 (1H, d, 17.01 Hz), 3.74 (1H, d, 17.04), 4.92 (1H, s), 5.32 (1H, s), 7.10–7.30 (4H, m); rac-isomer: 1.2–3.3 (16H, m), 2.04 (3H, s), 2.22 (3H, s), 3.53 (1H, d, J17.01 Hz), 3.79 (1H, d, 17.04), 4.88 (1H, s), 5.30 (1H, s), 7.10–7.30 (4H, m).

DCI-MS: m/z 604 (negative ions, peak with the highest cluster intensity).

Examples 7 to 16
Copolymerization of Ethylene with MAO as Cocatalyst.

Examples 7 to 12 refer to a series of copolymerization tests for the preparation of elastomeric polymers of the EPR type based on ethylene/propylene, carried out using a catalytic system comprising one of the metallocene complexes obtained as described above in examples 3 and 4, and methylalumoxane (MAO) as cocatalyst. In examples 13 to 16, a comparison is made in the production of the same copolymers using a catalytic system consisting one of the metallocene complexes, prepared according to example 2, and MAO as cocatalyst. The specific polymerization conditions of each example and the results obtained are indicated in table (I) below, which indicates in succession, the reference example number, the metallocene complex used, the quantity of zirconium used, the atomic ratio between the aluminum in the MAO and the zirconium in the metallocene, the total pressure and the polymerization temperature, the activity of the catalytic system expressed as kilograms of polymer per gram of metallic zirconium per hour: ($kg_{pol.}/g_{Zr} \times h$), the relative quantity, by weight, of the $C_3$ monomeric units in the polymer, the weight average molecular weight $M_w$ and the molecular weight dispersion $M_w/M_n$.

The polymerization is carried out in an 0.5 litre pressure reactor, equipped with a magnetic drag anchor stirrer and external jacket connected to a heat exchanger for the temperature control. The reactor is previously flushed, by keeping it under vacuum (0.1 Pascal) at a temperature of 80° C. for at least 2 hours.

130 g of "polymerization grade" liquid propylene are charged into the reactor at 23° C. The reactor is then brought to the desired polymerization temperature, generally ranging from 40° to 50° C. and "polymerization grade" gaseous ethylene is subsequently fed, by means of a plunged pipe, until the desired total equilibrium pressure is reached (2.2–3.0 MPa). Under these conditions, the molar concentration of ethylene in the liquid phase ranges from 12 to 18%, depending on the total pressure and temperature of the system, as can be easily calculated using suitable liquid-vapour tables.

MAO, as a 1.5 M (as Al) solution in toluene, and the desired quantity of one of the above metallocene complexes as a toluene solution generally having a concentration ranging from $3 \times 10^{-4}$ to $1 \times 10^{-3}$ M, are charged into a suitable tailed test-tube, maintained under nitrogen. The catalyst solution thus formed is kept at room temperature for a few minutes and is then transferred under a stream of inert gas to a metal container from which it is charged into the reactor, by means of nitrogen overpressure.

The polymerization reaction is carried out at the desired temperature, care being taken to keep the total pressure constant by continuously feeding ethylene to compensate the reacted part. After 15 minutes, the feeding of ethylene is interrupted and the polymerization is stopped by rapid degassing of the residual monomers. The polymer is recovered, after washing it with ethyl alcohol and drying at 60° C., at a reduced pressure of 1000 Pa, for at least 8 hours, in order to completely eliminate any possible residual monomers. The solid thus obtained is weighed and the catalytic activity is calculated as described above. The content of $C_3$ monomeric units is measured on the dried, homogenized solid, using the known techniques based on IR spectroscopy, together with the weight average molecular weight ($M_w$) and number average molecular weight ($M_n$). The results are indicated in table I.

TABLE I copolymerization of ethylene according to examples 7 to 16. The complex IVr forms part of the present invention, the others being provided for comparative purposes.

| Ex. Nr | Compl. | Zr (moles × $10^{-6}$) | Al/Zr m/m | $P_{Tot.}$ (MPa) | T (° C.) | Activity $Kg_{pol}/g_{Zr} \times h$ | $C_3$ (weight %) | $M_w$ (×$10^3$) | $M_w/M_n$ |
|---|---|---|---|---|---|---|---|---|---|
| 7 | IVr | 0.57 | 2800 | 2.2 | 40 | 3010 | 49.7 | 316 | 2.2 |
| 8 | IVr | 0.30 | 4700 | 2.5 | 40 | 4750 | 41.9 | 404 | 2.2 |
| 9 | IVr | 0.19 | 6100 | 3.0 | 50 | 6750 | 41.9 | 295 | 2.3 |
| 10 | IVm | 0.36 | 4050 | 2.2 | 40 | 1470 | 25.4 | 191 | 2.7 |
| 11 | IVm | 0.24 | 4800 | 2.5 | 40 | 2030 | 21.3 | 228 | 2.6 |
| 12 | IIIr | 0.61 | 4400 | 2.2 | 40 | 2680 | 47.9 | 238 | 1.9 |
| 13 | IIIr | 0.42 | 5500 | 2.5 | 40 | 3970 | 39.5 | 290 | 1.9 |
| 14 | IIIr | 0.22 | 6000 | 3.0 | 50 | 5180 | 40.1 | 98 | 2.0 |
| 15 | IIIm | 0.59 | 4500 | 2.2 | 40 | 2610 | 47.0 | 264 | 1.9 |
| 16 | IIIm | 0.45 | 5200 | 2.5 | 40 | 4080 | 31.8 | 326 | 1.9 |

Comments on Table I

As can be seen from Table I, the use of complexes with hydrogenated indenyl ligands [rac-o-benzylidenebis-($\eta^5$-1-tetrahydroindenyl)zirconium dichloride (IVr) and meso-obenzylidenebis-($\eta^5$-1-tetrahydroindenyl) zirconium dichloride (IVm)] in the production of elastomeric copolymers of the EPR type, causes considerable differences with respect to the use of analogous non-hydrogenated complexes (IIIr) and (IIIm). Under the same operating conditions, in fact, it is possible to obtain copolymers having a similar composition (examples 7 and 8 against 12 and 13) but with an activity and weight average molecular weights 15–20% higher. This latter fact also allows the complex of the present invention (IVr) to be used at higher temperatures which leads (example 9 against 8) to a considerable increase in the activity, the composition of the copolymer obtained remaining unvaried, whereas the weight average molecular weight value is still maintained at values of industrial interest. The use of the complex IIIr under analogous conditions (example 14) gives rise to the formation of copolymers having weight average molecular weights which are too low and therefore not suitable for normal use. Another characteristic can be observed considering that the complex rac-o-benzylidenebis-($\eta^5$-1-tetrahydroindenyl)zirconium dichloride (IVr) proves to be preferable with respect to the analogous meso isomer (IVm), as, under the same experimental conditions, it is capable of producing copolymers with a greater comonomer content, a higher weight average molecular weight value, with a catalytic activity over two times higher (examples 7–8 against 10–11).

Examples 17–22
Ethylene/propylene/ethylidene-norbornene (ENB) Terpolymerization Using MAO as Cocatalyst.

Examples 17 to 20 refer to a series of terpolymerization tests for the preparation of EP(D)M-type elastomeric polymers based on ethylene/propylene/ethylidene-norbornene (ENB), with a medium diene (ENB) content (5–7% by weight), carried out using a catalytic system comprising one of the metallocene complexes, obtained as described above in exampies 3 and 4, and methylalumoxane (MAO) as cocatalyst. In examples 21 and 22, a comparison is made in the production of the EP(D)M terpolymers, using, under analogous conditions, one of the complexes prepared according to example 2, and MAO as cocatalyst. The specific polymerization conditions of each example and the results obtained are indicated in table (II) below, which indicates in succession, the reference example number, the metallocene complex used, the quantity of zirconium used, the atomic ratio between the aluminum in the MAO and the zirconium in the metallocene, the total polymerization pressure, the initial concentration of ENB, the activity of the catalytic system expressed as kilograms of polymer per gram of metallic zirconium per hour: ($kg_{pol}/g_{Zr} \times h$), the relative quantity, by weight, of the $C_3$ monomeric units and ENB in the polymer, the weight average molecular weight $M_w$ and the molecular weight dispersion $M_w/M_n$.

The polymerization is carried out in an 0.5 litre pressure reactor, equipped with a magnetic drag anchor stirrer and external jacket connected to a heat exchanger for the temperature control. The reactor is previously flushed, by keeping it under vacuum (0.1 Pascal) at a temperature of 80° C. for at least 2 hours.

120 g of "polymerization grade" liquid propylene and the ENB diene, in such a quantity as to obtain the molar concentration indicated in the corresponding column in table (II) below, are charged into the reactor at 23° C. The reactor is then brought to the desired polymerization temperature of 40° and "polymerization grade" gaseous ethylene is subsequently fed, by means of a plunged pipe, until the desired total equilibrium pressure is reached (2.0–2.7 MPa). Under these conditions, the molar concentration of ethylene in the liquid phase ranges from 11 to 23%, depending on the total pressure and temperature of the system, as can be easily calculated using suitable liquid-vapour tables.

MAO, as a 1.5 M (as Al) solution in toluene, and the desired quantity of one of the above metallocene complexes as a toluene solution generally having a concentration ranging from $3 \times 10^{-4}$ to $1 \times 10^{-3}$ M, are charged into a suitable tailed test-tube, maintained under nitrogen. The catalyst solution thus formed is kept at room temperature for a few minutes and is then transferred under a stream of inert gas to a metal container from which it is charged into the reactor, by means of nitrogen overpressure.

The polymerization reaction is carried out at 40° C., care being taken to keep the total pressure constant by continuously feeding ethylene to compensate the reacted part. After 15 minutes, the feeding of ethylene is interrupted and the polymerization is stopped by rapid degassing of the residual monomers. The polymer is recovered, after washing it with ethyl alcohol and drying at 60° C., at a reduced pressure of 1000 Pa, for at least 8 hours, in order to completely eliminate any possible residual monomers. The solid thus obtained is weighed and the catalytic activity is calculated as described above. The content of the various $C_3$ monomeric units and ENB is measured on the dried and homogenized solid, using the known techniques based on IR spectroscopy, together with the weight average molecular weight ($M_w$) and number average molecular weight ($M_n$). The results are indicated in table II.

TABLE II terpolymerization of ethylene according to examples 17 to 22. The complex IVr forms part of the present invention, the others being provided for comparative purposes.

| Ex. Nr. | Compl. | Zr (moles × $10^{-6}$) | Al/Zr m/m | $P_{Tot}$ MPa | $ENB_{fed}$ moles % | Activ. $Kg_{pol.}/g_{Zr} \times h$ | C3 weight % | ENB weight % | $M_w \times 10^3$ | $M_w/M_n$ |
|---|---|---|---|---|---|---|---|---|---|---|
| 17 | IVr | 0.42 | 4400 | 2.5 | 0.8 | 3350 | 40.1 | 6.6 | 308 | 2.1 |
| 18 | IVr | 0.31 | 4000 | 2.7 | 0.8 | 3840 | 37.0 | 5.9 | 323 | 2.3 |
| 19 | IVm | 0.99 | 3200 | 2.0 | 1.6 | 170 | 30.5 | 6.7 | 89 | 2.1 |
| 20 | IVm | 0.72 | 4000 | 2.2 | 1.6 | 620 | 25.9 | 6.0 | 124 | 2.2 |
| 21 | IIIr | 0.53 | 4000 | 2.5 | 0.8 | 2600 | 38.1 | 5.0 | 269 | 1.8 |
| 22 | IIIm | 0.59 | 3900 | 2.5 | 0.8 | 2000 | 34.8 | 3.4 | 279 | 1.8 |

Comments on Table II

As can be seen from the data indicated in Table II, the use of the complex rac-o-benzylidenebis-($\eta^5$-1-tetrahydroindenyl)zirconium dichloride (IVr) also proves to be the preferred catalytic precursor for the production of EP(D)M-type terpolymers with a medium ENB content (5–7% by weight, examples 17–18). The analogous complexes, in fact, with non-hydrogenated indenyl ligands, (IIIr) and (IIIm), used under the same conditions, produce terpolymers with a lower diene quantity than that desired (examples 21–22). Furthermore on using the complex meso-o-benzylidenebis-($\eta^5$-1-tetrahydroindenyl)zirconium dichloride (IVm), it is only possible to obtain terpolymers with the desired diene quantity by operating with a double concentration of ENB, which leads to a drastic lowering of the catalytic activity (examples 19–20).

Finally, if other aspects are also considered, apart from the capacity of inserting ENB, it is evident that the complex (IVr) also remains preferable from the point of view of catalytic activity, the insertion of propylene and the production of terpolymers with higher weight average molecular weights.

Examples 23–31
Ethylene/propylene/ethylidene-norbornene (ENB) Terpolymerization using MAO as Cocatalyst.

Examples 23 to 29 refer to a series of terpolymerization tests for the preparation of EPDM-type elastomeric polymers based on ethylene/propylene/ethylidene-norbornene (ENB) with a high (>10% by weight) diene (ENB) content, carried out using a catalytic system comprising the metallocene complex, obtained as described above in example 3 above, and methylalumoxane (MAO) as cocatalyst. In examples 30 and 31, a comparison is made in the production of the EPDM terpolymers, using, under analogous conditions, one of the complexes prepared according to example 2, and MAO as cocatalyst. The specific polymerization conditions of each example and the results obtained are indicated in table (III) below, which indicates in succession, the reference example number, the metallocene complex used, the quantity of zirconium used, the atomic ratio between the aluminum in the MAO and the zirconium in the metallocene, the total polymerization pressure, the initial concentration of ENB, the activity of the catalytic system expressed as kilograms of polymer per gram of metallic zirconium per hour: ($kg_{pol}/g_{Zr} \times h$), the relative quantity, by weight, of the $C_3$ monomeric units and ENB in the polymer, the weight average molecular weight $M_w$ and the molecular weight dispersion $M_w/M_n$.

The procedure for the polymerization, the preparation of the catalytic system and recovery of the polymer obtained, are analogous to those described above in examples 17–22.

TABLE III copolymerization of ethylene according to examples 23 to 31. The complex IVr forms part of the present invention, the others being provided for comparative purposes.

| Ex. Nr. | Compl. | Zr (moles × $10^{-6}$) | Al/Zr m/m | $P_{Tot.}$ MPa | $ENB_{fed}$ moles % | Activ. $Kg_{pol}/g_{Zr} \times h$ | $C_3$ weight % | ENB weight % | $M_w \times 10^3$ | $M_w/M_n$ |
|---|---|---|---|---|---|---|---|---|---|---|
| 23 | IVr | 0.61 | 3500 | 2.2 | 0.8 | 1420 | 49.2 | 10.5 | 120 | 3.4 |
| 24 | IVr | 1.10 | 2800 | 2.0 | 1.6 | 540 | 53.3 | 16.7 | 105 | 1.8 |
| 25 | IVr | 0.67 | 3200 | 2.2 | 1.6 | 800 | 48.6 | 12.7 | 107 | 2.2 |
| 26 | IVr | 0.61 | 3100 | 2.5 | 1.6 | 1550 | 39.9 | 10.7 | 290 | 2.2 |
| 27 | IVr | 0.61 | 3100 | 2.7 | 1.6 | 1960 | 36.8 | 10.4 | 340 | 2.1 |
| 28 | IVr | 0.98 | 3100 | 2.5 | 2.0 | 990 | 40.9 | 13.3 | 214 | 1.9 |
| 29 | IVr | 1.10 | 2900 | 2.5 | 2.4 | 440 | 47.1 | 16.1 | 119 | 1.8 |
| 30 | IIIr | 0.55 | 2900 | 2.5 | 1.6 | 1630 | 36.1 | 7.3 | 272 | 1.8 |
| 31 | IIIm | 0.57 | 3000 | 2.5 | 1.6 | 1490 | 35.9 | 5.8 | 288 | 2.0 |

Comments on Table III

The data provided in Table III indicate that only by using the complex rac-o-benzylidenebis-($\eta^5$-1-tetrahydroindenyl) zirconium dichloride (IVr) is it possible to obtain terpolymers with a high diene content (examples 23–29). Operating under the conditions described, it is in fact only possible to produce terpolymers with ENB values higher than 16% by weight, using (IVr) as catalytic precursor. Particularly significant are examples 26 and 27 that summarize the experimental conditions for obtaining terpolymers, which from the point of view of composition and average molecular weight value, prove to be in line with the characteristics of analogous industrial products.

What is claimed is:

1. Metallocene compounds of formula (I) having a racemic stereoisomerism

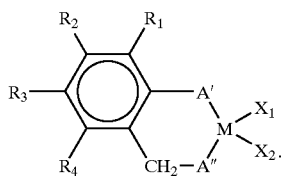

(I)

wherein
M is selected from zirconium and hafnium;
$X_1$ and $X_2$, the same or different, are selected from halogen, amide, carboxy, alkoxy, carbamate, alkyl, aryl, hydrogen;

A' and A", the same or different, are a radical of the $\eta^5$-tetrahydroindenyl type (Ia):

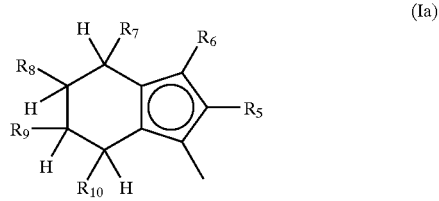

(Ia)

wherein the groups $R_5$, $R_6$, $R_7$, $R_8$, $R_9$, $R_{10}$, the same or different, are selected from hydrogen, a $C_1$–$C_8$ aliphatic, $C_5$–$C_{12}$ cycloaliphatic, $C_6$–$C_{14}$ aryl radical;
the groups $R_1$, $R_2$, $R_3$, $R_4$, the same or different, are selected from hydrogen, a $C_1$–$C_8$ aliphatic, $C_5$–$C_{12}$ cycloaliphatic, $C_6$–$C_{14}$ aryl radical, halogen.

2. The metallocene compounds according to claim 1, wherein $X_1$ and $X_2$, the same or different, are selected from halogen, a $C_1$–$C_7$ hydrocarbyl radical, hydrogen.

3. The metallocene compounds according to claim 2, wherein $X_1$ and $X_2$ are chlorine.

4. The metallocene compounds according to claim 1, wherein $R_5$, $R_6$, $R_7$, $R_8$, $R_9$, $R_{10}$, the same or different, are selected from hydrogen, methyl, ethyl, phenyl.

5. The metallocene compounds according to claim 1, wherein $R_1$, $R_2$, $R_3$, $R_4$, the same or different, are selected from hydrogen, methyl, benzyl, fluorine.

6. The metallocene compounds according to claim 5, wherein $R_1=R_2=R_3=R_4=H$.

7. A metallocene compound according to claim 1, having a raceimc-type stereoisomerism, wherein groups $R_1$–$R_{10}$ are all equal to H, M=Zr, $X_1=X_2=Cl$.

8. A process for the preparation of ethylene-propylene (EPR) elastomeric copolymers having a propylene content ranging from 15 to 75% by weight, which comprises the following steps:

(1) propylene, optionally diluted with a hydrocarbon, is fed to a polymerization reactor, at such a pressure as to allow the use of propylene in liquefied form;

(2) ethylene is added to the mixture obtained in step (1) in a sufficient quantity to maintain a desired ethylene/propylene ratio in liquid phase;

(3) a catalytic system is added to the mixture obtained in step (2), said catalytic system comprising one or more metallocenes according to claim 1 having general formula (I) and one or more co-catalysts selected from (i) compounds having general formula (IV) $(Ra)_xNH_{4-x}B(Rd)_4$, compounds having general formula (V) $(Ra)_3PHB(Rd)_4$, compounds having general formula (VI) $B(Rd)_3$, compounds having general formula (VII) $(C_6H_5)_3CB(Rd)_4$, optionally in the presence of an alkylating agent, (ii) an alumoxane; in the above compounds having general formula (IV),(V), (VI) or (VII), x being selected from 1, 2 or 3; the groups $R_a$, the same or different, being monofunctional alkyl or aryl groups; the groups $R_d$, the same or different, being monofunctional aryl radicals;

(4) the mixture obtained in step (3) is reacted for a sufficient time to allow the polymerization of the ethylene-propylene system to give an EPR copolymer.

9. A process for the preparation of ethylene-propylene-diene (EPDM) elastomeric terpolymers, which comprises the following steps:

(1) propylene and the diene, optionally diluted with a hydrocarbon, are fed to a polymerization reactor, at such a pressure as to allow the use of propylene in liquefied form;

(2) ethylene is added to the mixture obtained in step (1) in a sufficient quantity to maintain a desired ethylene/propylene/diene ratio in liquid phase;

(3) a catalytic system is added to the mixture obtained in step (2), said catalytic system comprising one or more metallocenes according to claim 1 having general formula (I) and one or more co-catalysts selected from (i) compounds having general formula (IV) $(Ra)_xNH_{4-x}B(Rd)_4$, compounds having general formula (V) $(Ra)_3PHB(Rd)_4$, compounds having general formula (VI) $B(Rd)_3$, compounds having general formula (VII) $(C_6H_5)_3CB(Rd)_4$, optionally in the presence of an alkylating agent, (ii) an alumoxane; in the above compounds having general formula (IV), (V), (VI) or (VII), x being selected from 1, 2 or 3; the groups $R_a$, the same or different, being monofunctional alkyl or aryl groups; the groups $R_d$, the same or different, being monofunctional aryl radicals;

(4) the mixture obtained in step (3) is reacted for a sufficient time to allow the polymerization of the ethylene-propylene-diene system to give an EPDM terpolymer.

10. The process according to claim 8, wherein in step (1) propylene diluted with a hydrocarbon is fed to the polymerization reactor.

11. The process according to claim 8, wherein in step (1) propylene diluted with a low-boiling $C_3$–$C_5$ hydrocarbon is fed to the polymerization reactor.

12. The process according to claim 8, wherein in step (1) propylene diluted with propane is fed to the polymerization reactor.

13. The process according to claim 9, wherein in step (1) propylene and the diene diluted with a hydrocarbon is fed to the polymerization reactor.

14. The process according to claim 9, wherein in step (1) propylene and the diene diluted with a low-boiling $C_3$–$C_5$ hydrocarbon is fed to the polymerization reactor.

15. The process according to claim 9, wherein in step (1) propylene and the diene diluted with propane is fed to the polymerization reactor.

16. The process according to claim 8, wherein M is zirconium.

17. The process according to claim 8, wherein M is hafnium.

18. The process according to claim 9, wherein M is zirconium.

19. The process according to claim 9, wherein M is hafnium.

20. The compounds according to claim 1, wherein M is zirconium.

21. The compounds according to claim 1, wherein M is hafnium.

22. The compounds according to claim 2, wherein M is zirconium.

23. The compounds according to claim 2, wherein M is hafnium.

24. The compounds according to claim 3, wherein M is hafnium.

25. The compounds according to claim 3, wherein M is zirconium.

26. The compounds according to claim 4, wherein M is hafnium.

27. The compounds according to claim 4, wherein M is zirconium.

28. The compounds according to claim 5, wherein M is hafnium.

29. The compounds according to claim 5, wherein M is zirconium.

30. The compounds according to claim 6, wherein M is hafnium.

31. The compounds according to claim 6, wherein M is zirconium.

* * * * *